United States Patent
Chelle et al.

(10) Patent No.: US 9,669,100 B2
(45) Date of Patent: Jun. 6, 2017

(54) POLYMER SUPPORT FOR THE DISTRIBUTION OF A NATURALLY CRYSTALLINE SUBSTANCE AND PRODUCTION METHOD

(71) Applicant: AB7 INNOVATION S.A.S.U., Grepiac (FR)

(72) Inventors: Rene Chelle, Grepiac (FR); Arnaud Vilbert, Baziege (FR)

(73) Assignee: AB7 INNOVATION S.A.S.U., Deyme (FR)

( * ) Notice: Subject to any disclaimer, the term of this patent is extended or adjusted under 35 U.S.C. 154(b) by 0 days.

(21) Appl. No.: 14/767,707

(22) PCT Filed: Feb. 10, 2014

(86) PCT No.: PCT/FR2014/000032
§ 371 (c)(1),
(2) Date: Aug. 13, 2015

(87) PCT Pub. No.: WO2014/125175
PCT Pub. Date: Aug. 21, 2014

(65) Prior Publication Data
US 2015/0374829 A1 Dec. 31, 2015

(30) Foreign Application Priority Data
Feb. 15, 2013 (FR) .................... 13 00330

(51) Int. Cl.
| A61K 47/34 | (2017.01) |
| A61K 31/522 | (2006.01) |
| A01N 25/10 | (2006.01) |
| A01N 25/34 | (2006.01) |
| A01N 53/00 | (2006.01) |
| A01K 27/00 | (2006.01) |
| C08J 3/205 | (2006.01) |

(52) U.S. Cl.
CPC ............ *A61K 47/34* (2013.01); *A01K 27/007* (2013.01); *A01N 25/10* (2013.01); *A01N 25/34* (2013.01); *A01N 53/00* (2013.01); *A61K 31/522* (2013.01); *C08J 3/2053* (2013.01); *C08J 2375/08* (2013.01); *C08J 2377/00* (2013.01)

(58) Field of Classification Search
CPC ........ A01N 25/10; A01N 53/00; A01N 25/34; A01N 25/02; A01K 27/007; A61K 31/522; A61K 47/34; C08J 2375/08; C08J 2377/00; C08J 3/2053
See application file for complete search history.

(56) References Cited

FOREIGN PATENT DOCUMENTS

| EP | 0436428 A1 | 7/1991 | |
| EP | 0539295 A1 | 4/1993 | |
| EP | 0671123 A1 | 9/1995 | |
| WO | 2007085615 A1 | 8/2007 | |
| WO | WO2007/085615 A1 * | 8/2007 | .............. A61K 9/16 |

OTHER PUBLICATIONS

International Search Report PCT/FR2014/000032; May 2, 2014; Nicola Costantini.

* cited by examiner

*Primary Examiner* — Audrea Buckley
(74) *Attorney, Agent, or Firm* — Klauber & Jackson LLC

(57) ABSTRACT

The invention relates to the implementation of a method for loading, without a vehicle, a naturally crystalline substance solubilized by a solvent mixture in a lipophilic medium in a mixture of granulated polymers, for forming, without a plasticizer, a polymer support for the long-term controlled distribution of the naturally crystalline substance in the stable solubilized state, without permanent crystallization on the surface of said support. Said substance according to the invention can be insecticides and pesticides of the group of pyrethroids (e.g. deltamethrin), formamidines (e.g. amitraz) and carbamates (e.g. propoxur), or the mixture thereof, or cosmetics of the group of alkaloids (e.g. caffeine), or medicaments (e.g. ibuprofen). The permanent non-crystallization state on the surface of the polymer support is only ensured when said substance is solubilized in the solvent mixture consisting of an oxygenated solvent of dibasic esters of methylenic fatty acids and an oxygenated methylenic cosolvent in an active lipophilic solution incorporated into a polymer mixture consisting of a polyether block amide (PEBA) and a thermoplastic polyurethane elastomer (TPU). Said support can be shaped as a collar, as an ear tag for animals, a band, a patch, a tag, a polymer block or any other device for the distribution of the active substances. It is shaped by any one of the plastic processing techniques known by a person skilled in the art. It is advantageous in that it is loaded with a quantity of active substance of between 30% and 50% less than the previous devices for at least the same active efficiency.

20 Claims, 1 Drawing Sheet

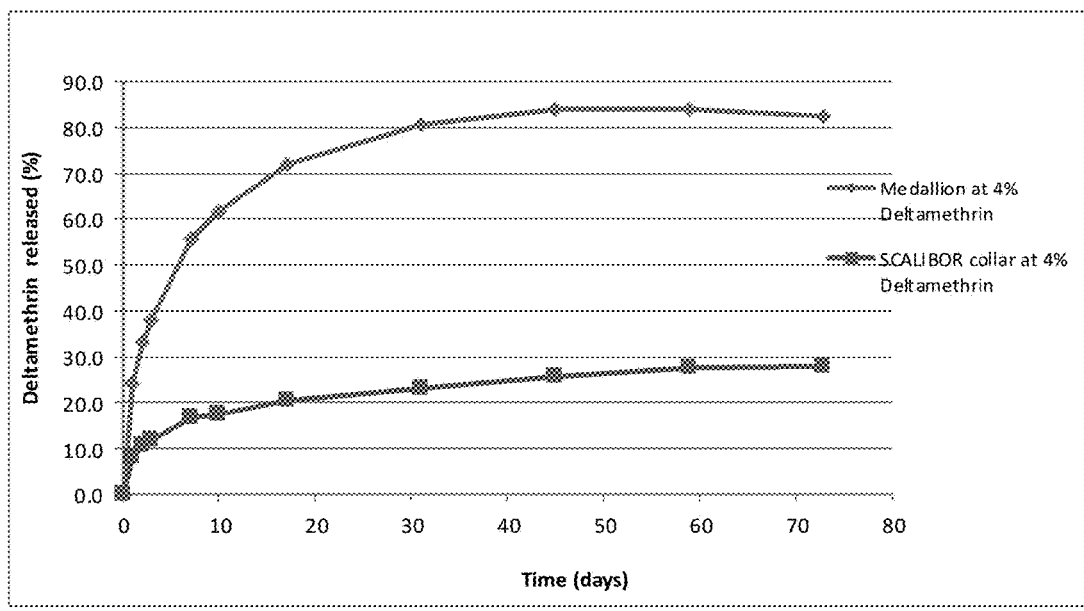

POLYMER SUPPORT FOR THE DISTRIBUTION OF A NATURALLY CRYSTALLINE SUBSTANCE AND PRODUCTION METHOD

The invention relates to the production of a polymer support for the distribution of a naturally crystalline substance in the solubilised state without crystallization on the surface.

The purpose of this invention is to implement a method for loading, without a vehicle, a naturally crystalline substance solubilised by a solvent mixture in a lipophilic medium in a mixture of polymer pellets intended for forming, without a plasticizer, a polymer support for the long-term controlled distribution of the naturally crystalline substances in the stable solubilized state without permanent crystallization on the surface of the said support.

It is known as described in the French patent FR 2 746 261 B1 (VIRBAC S.A.—19 Mar. 1996) that the insecticides of the group of pyrethroids, formamidines and carbamates are lipophilic substances particularly sensitive to hydrolysis under given pH conditions and are completely incompatible with the aqueous environment, especially formamidines. Crystallization is known as the form of physical instability, particularly for pyrethroids and some concentrated compositions; it is doubled by chemical instability, essentially for some main active substances, such as carbamates and formamidines.

Likewise, in cosmetics, alkaloids pose particularly a problem of crystallization linked to temperature and concentration conditions. It is the case, for example, with caffeine, which must have a low content in a gelled medium to be applicable to the skin.

Some drugs also fall into this category, such as ibuprofen, which must be formulated at 5% specifically in a gel for skin application. The gel prevents a crystallization of the active substance on the skin, which would hinder its transdermal passage.

These naturally crystalline chemical substances solubilised and then incorporated into a solid support systematically recrystallize on the surface of said support as soon as the solute/solvent ratio is modified by the evaporation of said solvent or by a chromatographic effect due to the nature of the matrix containing them. Without being exhaustive, the said polymer support may be in the shape of a collar, bracelet, ear tag, medallion or patch. This phenomenon makes it difficult to realize controlled distribution devices of the aforementioned substances from the solid supports impregnated with them.

The patent EP0539295 (RUSSEL-UCLAF—22 Oct. 1992) describes a controlled release device of Deltamethrin incorporated in a vinyl polymer matrix made of polyvinyl chloride (PVC). To alleviate the difficulties of the migration of the active substance within the matrix, a liquid plasticizer miscible in the polymer and triphenyl phosphate are used as a vehicle for the active substance. The active substance is mixed with its vehicle, which allows its migration within the matrix to the surface of the device. However, in the end, the active substance is always recrystallized on the surface of the device.

This system, which implicates a combination of two binomes that must be compatible, formed by a compatible polymer and plasticizer, on the one hand, and an active liquid or solid substance and its vehicle, on the other hand, allows incorporating and maintaining the said active substance in a polymer support. It is a technical solution which has been used a lot in many fields for the controlled distribution of an active crystalline substance or an association of active crystalline substances controlled in the long-term from a polymer support. Here is a non-exhaustive list of patents, which resort to it and describe it well. For example: EP0052411 B1 (ZOECON CORPORATION—10 Apr. 1981), EP0090446 A2 (SHELL INTERNATIONAL RESEARCH—15 Mar. 3, 1983), EP0436428 B1 (LABORATOIRES VIRBAC—21 Dec. 1990), EP0537998 B1 (MERCK & Co., Inc.—14 Oct. 1992), EP0539295 B1 (ROUSSEL-UCLAF—22 Oct. 1992), EP0542080 B1 (BAYER AG—2 Nov. 1992), EP0671123 B1 (ZOBELE INDUSTRIE CHIMICHE S.p.A.—11 Mar. 1994) and EP1022944 B1 (AKZO NOBEL N.V.—16 Jun. 1998).

The resins and polymers used to realize the devices described in these patents are varied and often have a linear structure. Many of them cannot be shaped as desired without the presence of a compatible plasticizer. Because they are unable to incorporate active substances within the matrices formed to deliver these active substances in a long-term controlled distribution, vehicles of the active substances have to be added to them. Without being exhaustive, here are a few examples: vinyl polymers, preferably polyvinyl chloride and its copolymers with vinyl acetate and vinylidene dichloride, polypropylene, polyamide, polycarbonates, polystyrene, polyesters such as cellulose acetate, polylactide, cellophane, as well as the mixture of all these polymers, polyethylene, ethylene/vinyl acetate copolymers, polyester- and polyether-based polyurethane, or glycol ether/terephthalate ester copolymers and other thermoplastic elastomers.

Plasticizers intended for the functional adaptation of the physical properties of polymers are chosen from among phosphoric acid esters, phthalic esters commonly called phthalates, adipic acids, etc. Phthalates are substances currently prohibited or to be shortly prohibited for many applications due to their toxicity level. Other plasticizers migrate within the matrix and consequently present a risk of passage on the skin or through the skin.

The vehicles of active substances have the function of storing the active substance and promoting its migration within the polymer matrix in which the said vehicles are incorporated. To do this, a good compatibility has to exist between the vehicle and the polymer matrix. The vehicles of active substances are generally chosen from among mineral fillers, such as triphenyl phosphate. It should be noted that some fillers could embrittle or modify the physical properties of the polymer matrix. In a case where coalescence is sought for the transfer of the active substance to the polymer support (EP0537998 B1), the following vehicles were used: an ether, polyethylene glycol or alkoxylated polyethylene glycol, a polypropylene glycol, a polyethylene glycol/polypropylene glycol, crosslinked polymer, an ethoxylated alkyl phenol, or a fatty ester, ethoxylated sorbitan. Likewise, polyisocyanates were used as a vehicle of active substances in the French patent FR 2746261 B1 (VIRBAC S.A.—19 Mar. 1996). Products functioning by coalescence have the disadvantage of having a high instability in storage.

All these solutions developed in the prior art are far from a cure-all to guarantee a regular transfer of an active substance in a solid support in order to ensure without denaturation and in a stable manner, without the appearance of crystallization, an extended, controlled distribution to a target external to the said support. The most common physical instability of active solutions incorporated in a polymer support is the crystallization of the active molecules on the surface of said support observed on most products described in the prior art. This phenomenon is due to the concentration threshold of the said molecules in direct relation with the solute/solvent ratio, which, by changing in favour of the solute for a higher concentration, is the origin of the instability expressed by crystallization. Crystallization remains a major disadvantage when the following devices are used: bracelets, collars and ear tags for animals, patches, and other polymer blocks or packs. It is the cause of a loss of substance, a physical loss due to the unbinding of the crystals of the support and a chemical loss due to the denaturation of the molecules. It slows down and reduces as such the effective action of the active substance because the crystals cannot pass directly through the dermal barrier and hardly in the suint or sebum of animals.

To avoid all the problems inherent to the methods of incorporating a naturally crystalline active substance into a polymer support, such as those described in the prior art, the patent application US 2011/0256195A1 (Bayer Crop Science AG—14 Apr. 2011) adopts mixing the polymer and the active substance at the high temperature of 250° C. It is recognized that at this temperature the active substance is in a molten state like the polymer, thereby obtaining a good active substance/polymer mixture, but unfortunately offers only a minimum guarantee on the chemical integrity of the active substance.

In the patent application WO 2007/085615A1 (BIOCOMPATIBLES UK LIMITED—24 Jan. 2007), to prevent the crystallization of the supported active substance, a method is applied which uses crystallization inhibiter agents such as glycols, glycol esters, iodized soya bean oil, iodized sunflower oil, or iodized poppy seed oil. The said inhibiter agents are dissolved with the crystalline active substance in a volatile organic solvent. The said solvent is an alcohol, ethanol or propanol. In this method, the excess solvent is eliminated from the polymer matrix by evaporation or sublimation, which poses a recurrent environmental problem for the use of volatile solvents. The polymer matrix in the form of microspheres is an ethylene/polyvinyl alcohol copolymer which must be anionic. This last property is obtained by adding buffered carboxylate, phosphonate, or sulfonate groups. The method claimed in this application is complex to realize, which is a major disadvantage because it increases the product cost. It can also lead to environmental problems.

The method of this invention allows compensating for the disadvantages of the prior art. In fact, it allows realizing more simply incorporation without vehicle, naturally crystalline substances into a polymer support whose matrix is shaped without plasticizer. It is based on the technology of active polymers developed by the applicant and concretized among others by the patent FR 2 901 172 B1 (18 May 2006) titled "Procédé chargement à froid d'un actif dans une matrice polymère" (Method for loading polymer matrix in low temperature with active principle).

The term "solvent mixture" designates the mixture of a solvent with a cosolvent, which allows obtaining a complete, permanent solubilisation of the naturally crystalline substance.

The term "naturally crystalline substance", in singular or plural form, designates an active naturally crystalline substance or a mixture of several active naturally crystalline substances, or a mixture with at least one active naturally crystalline substance and at least one active naturally non-crystalline substance.

The term "polymer mixture" designates the mixture of at least two polymers according to a ratio defined to form a polymer matrix intended to obtain a polymer support according to the conventional techniques of plastics technology.

An object of the invention is a loading method without a vehicle of a naturally crystalline substance solubilised by a solvent mixture in a lipophilic medium into a mixture of polymer granules intended for forming without plasticizer a polymer support of a long-term controlled distribution in the stable solubilised state of the said substance without crystallization on the surface of said support.

According to an embodiment of the invention, the method is characterized in that the solubilised state of the naturally crystalline substance is obtained surprisingly by using a solvent mixture composed of an oxygenated solvent of dibasic esters of methylenic fatty acids, which is associated with an oxygenated methylenic cosolvent.

According to another embodiment of the invention, the solvent is a mixture of dibasic esters of methylenic fatty acids. It offers the advantage of being an oxygenated solvent with a low vapour pressure, and therefore practically non-volatile. Its dissolving efficiency of naturally crystalline substances is effective from the temperature of 45° C.

According to another embodiment of the invention, the cosolvent is an oxygenated methylenic solvent, dimethyl isosorbide (DMI), which is a non-toxic "green" solvent. Its dissolving efficiency of naturally crystalline substances is effective even at room temperature. It has a disadvantage, its high cost, which could limit its use on a large scale. Known to be a good emollient, it is chosen in this invention at a limited rate in order to associate to the solvent character a control character for a possible transdermal passage of the solubilized active substances.

According to an embodiment of the invention, the solvent mixture allows unexpectedly increasing the concentration threshold of the naturally crystalline substances for better dissolving. For example, a maximum of 20% by weight of a cold solution of Deltamethrin is possible without recrystallization in the active solution even at low temperature. Caffeine is dissolved in a stable manner in the said solvent mixture at 6% by weight of solution and Propoxur at 56% by weight of solution too.

The said solvent mixture according to the invention advantageously leads to a reduction on the order of 30% to 50% of the active substance quantity to be incorporated into the support with respect to prior devices, while attaining at least and if not better the active substance efficiency results. This advantageous property results from the perfect solubilized state of the active substance and the emollient character of the cosolvent.

According to the invention, the oxygenated solvent of dibasic esters of methylenic fatty acids taken alone does not offer these advantages. Likewise, the oxygenated methylenic solvent chosen as the cosolvent taken alone did not allow attaining the targeted objectives either.

Surprisingly, the ratio of the two components of the solvent mixture in the order solvent/cosolvent, which allows attaining the objectives according to the invention, varies between 38/62 and 90/10, preferably between 45/55 and 75/25.

According to an embodiment of the invention, the solubilised naturally crystalline substances can be insecticides and pesticides of the group of pyrethroids (e.g. Deltamethrin), formamidines (e.g. Amitraz) and carbamates (e.g. Propoxur) or a combination thereof, or cosmetics of the group of alkaloids (e.g. Caffeine), or drugs (e.g. Ibuprofen).

According to an embodiment of the invention, to obtain the lipophilic character of the medium, at least one vegetable oil chosen from among coconut oil, sweet almond oil, macadamia oil or any other vegetable oil accepted in cosmetics or pharmaceutical products is to be added to the naturally crystalline substance solution.

The said active lipophilic solution obtained according to the invention is incorporated into a polymer mixture. The thermoplastic polymers used within the framework of the invention are chosen from among the polyolefins and polyurethane elastomers.

Unexpectedly, the permanent non-crystallization state on the surface of the polymer support distributing naturally crystalline substances is only ensured when the said substances are solubilised in the solvent mixture composed of an oxygenated solvent of dibasic esters of methylenic fatty acids and an oxygenated methylenic cosolvent forming an active lipophilic solution by adding vegetable oil; this active lipophilic solution is incorporated into a polymer mixture composed of a polyether block amide (PEBA) and a thermoplastic polyurethane elastomer (TPU).

PEBA taken alone does not allow permanently ensuring the non-crystallization on the surface of the device of a naturally crystalline substance incorporated within it in the solubilized state. Likewise, TPU taken alone does not allow attaining this objective of the invention either.

Surprisingly, this objective according to the invention is attained when the ratio of the polymer mixture in the order PEBA/TPU varies between 80/20 and 40/60, preferentially between 55/45 and 45/55.

According to an embodiment of the invention, where appropriate, technical additives can be added in shaping of the support, such as colouring agents and/or structure polymers designed to adapt mechanical properties, such as the flexibility of the said support for its intended purpose, as well as other additives not interfering with the permanent non crystallization state on the surface of said support.

Another object of this invention is the polymer support of a long-term controlled distribution of the naturally crystalline substances in a stable solubilized state, without any permanent crystallization on its surface. The said support can be in the shape of a collar, medallion, ear tag for animals, bracelet, patch, pack, polymer block, or any other device to distribute the active substances. It is shaped by any one of the techniques of the plastics technology known by a person skilled in the art.

According to an embodiment of the invention, the support has a capacity to store between 0.25% and 20% by weight of a naturally crystalline substance according to the nature of the said substance and the intended purpose of the said support.

According to this invention, the loading method without a vehicle of a naturally crystalline substance solubilised by a solvent mixture in a lipophilic medium into a mixture of polymer granules intended for forming without plasticizer a polymer support of a long-term controlled distribution in the stable solubilised state of the said substance, the said method ensuring the permanent non-crystallization on the surface of said support, proceeds as follows:
 a) Preparation of the solvent mixture composed of an oxygenated solvent of dibasic esters of methylenic fatty acids and an oxygenated methylenic cosolvent;
 b) Solubilisation of the naturally crystalline substance in the solvent mixture obtained in step a) to obtain the stable solution of a naturally crystalline substance;
 c) Addition of vegetable oil in the solution obtained in b) to obtain an active lipophilic solution;
 d) Composition of the polymer mixture by associating the polyether block amide (PEBA) with a thermoplastic polyurethane elastomer (TPU);
 e) Incorporation of the active lipophilic solution obtained in c) into the polymer mixture obtained in d) to obtain the polymer mixture loaded with a naturally crystalline substance in the solubilised state;
 f) Where appropriate, addition of technical additives to the loaded polymer mixture obtained in e);
 g) Forming of the support loaded with a naturally crystalline substance in the solubilised state by treating the loaded polymer mixture obtained in f) by any one of the techniques of the plastics technology known by a person skilled in the art.

The support filled with a naturally crystalline substance in the solubilised state obtained with the method of the invention is necessarily put under a conservatory title in a sealed, preferably individual packaging for its storage before use.

According to an embodiment directly integrated to industry of the invention, the polymer support of a long-term controlled distribution of naturally crystalline substances in the stable solubilised state without crystallization on the surface of the said support under various shapes adapted to its use is produced in specific toolings of the techniques of plastics technology known by a person skilled in the art.

EXAMPLES

Example 1: Elaboration of an Anti-Ectoparasitic Polymer Medallion with Deltamethrin The following inputs are available:
 Oxygenated solvent of dibasic esters of methylenic fatty acids marketed by DOW HALTERMANN under the registered trademark ESTASOL®.
 Oxygenated methylenic solvent which is dimethyl isosorbide (DMI) marketed by CRODA under the registered trademark ARLASOLVE® DMI.
 Deltamethrin in powder form marketed by SIGMA ALDRICH under the registered trademark FULKA®.
 Refined coconut oil marketed by OLVEA.
 Polymer granules of polyether block amide (PEBA) marketed by ARKEMA under the registered trademark PEBAX® 2533 SA 01.
 Polymer granules of ether-based thermoplastic polyurethane (TPU) marketed by GAZECHIM under the registered trademark PEARLTHANE® D15N70.
 Pearly white colouring agent which is a masterbatch marketed by ELIAN.

The elaboration of an anti-ectoparasitic polymer medallion with Deltamethrin proceeds in three steps.

Step 1: Preparation of the Active Solution
 Preparation of the solvent mixture ESTASOL®/ARLASOLVE® DMI according to a ratio of 75%/25%
 Solubilisation of the Deltamethrin in the solvent mixture according to a ratio Deltamethrin/solvent mixture of 12.6%/87.4%;
 Addition of refined coconut oil according to an active ratio solvent mixture/coconut oil of 75%/25%.
Procedure:
In a 1 liter beaker, the following products are successively introduce with stirring:
 600 g ESTASOL®
 200 g ARLASOLVE® DMI
And then introduce by sprinkling while still stirring:
 115 g Deltamethrin
After completely dissolving, pour while still stirring:
 300 g refined coconut oil.
After 30 min, a stable, limpid active solution is obtained.

Step 2: Incorporation of the Active Solution into the Polymer Granules of PEBAX® 2533 SA 01/PEARLTHANE® D15N70

Procedure:

Preheat the DRAIS horizontal mixer having a volume of 20 liters, to 95° C.;

While stirring at 80 rpm, add 1843 g granules PEBAX® and 1843 g granules PEARLTHANE® D15N70, that is, a ratio of 50%/50%;

Let mix until the real temperature of the granules is 80° C.;

Still stirring, add drop by drop 1215 g of active solution to the mixer, that is, a ratio of active solution/polymer of 25%/75%;

Let the active solution incorporate into the polymer granules for approximately 30 minutes until they become dry and unsticky;

Lower the mixer temperature to 20° C. and the stirring speed to 50 rpm;

Still stirring, add 100 g of pearly white colouring agent;

Stop stirring after 20 minutes;

The resulting polymer granules loaded with the coloured active substance is collected.

Step 3: Forming by Injection-Molding in the Medallion to be Fastened to a Collar A SANDRETTO series 8 injection press developing a pressure capacity of 90 ton mould is available.

The steel mould mounted on the said press has four imprints-moulds in the shape of a medallion.

The temperature chart of the sheath from the hopper to the nozzle is as follows: 105° C., 125° C., 125° C., 25%.

The medallions loaded with Deltamethrin obtained weigh approximately 10 g and contain 2.4% Deltamethrin, that is, 40% less than the devices of the prior art. They have a main oval body equipped with a tab on one of the sides and a pass-through on the other.

The medallions loaded with Deltamethrin obtained are packaged and stored at room temperature for 12 months. No recrystallization of the Deltamethrin is observed at the medallion surface, proof that the Deltamethrin has remained in the solubilised state.

The medallion is fastened and mounted on a dog collar placing it in intimate contact with the fur, that is, directly with the animal skin.

The said medallion allows effectively fighting against ectoparasites of all kinds for a long period, that is, up to several months.

Example 2: Comparative Study of Releasing Deltamethrin in Olive Oil from a Support According to the Invention and from a Commercially Available Support Use of olive oil is known to determine the quantity of a solubilized non-volatile active substance released in a lipophilic composition. The choice of olive oil is justified by the fact that its composition is close to the structure of the lipid layer of the animal epidermis.

In fact, this experimental model which allows evaluating the quantity of Deltamethrin released from the medallion loaded with Deltamethrin obtained according to the method of the invention, as well as from a commercially available collar, the SCALIBOR® loaded with Deltamethrin.

Procedure:

Three medallions loaded with 4% Deltamethrin and each weighing approximately 10 g are placed in a 120 mm dia crystallizing dish in which 200 milliliters of olive oil are poured. The medium is stirred at 250 rpm using a magnetized bar placed in each crystallizing dish.

In parallel, the same protocol is performed with SCALIBOR® with 4% Deltamethrin each weighing approximately 25 g. Stirring is made at 250 rpm.

A standard solution at 40 mg/L Deltamethrin whose purity is known is realized under the same conditions using olive oil.

Protocol:

The released Deltamethrin quantity is determined by High Pressure Liquid Chromatography (HPLC). To do this, a PROVIDER ICS® chromatograph equipped with a pump model 2250 and a column PRONTOSIL® 120-5-C18 sized 250 mm×3.0 mm is available. A mobile phase of acetonitrile/water (85/15) is worked with and the detector's wavelength is adjusted to 275 nm.

5 milliliters samples of each solution are taken to start the chromatography and then completed with 5 milliliters of fresh olive oil after each sampling.

Samples are taken at times T0, T1, T2, T3, T7, T10, T17, T31, T45, T59, and T73. The time unit is a day. After each sampling, each sample is analysed by HPLC to determine the Deltamethrin quantity released in the olive oil.

The obtained results are shown on the graphic in FIG. 1 in terms of "Deltamethrin release kinetics in percentage in olive oil".

By referring to FIG. 1, it discloses that 65% more Deltamethrin is released by the support according to the invention than that released by the commercially available collar. This proves a clearly operational superiority with respect to the Deltamethrin quantity released by both devices.

Example 3: Elaboration of a Caffeine Patch to Fight Against Human Orange Skin

Thanks to its hydrophilic property, it is well known that caffeine is generally formulated in cream or in gel. Moreover, the largest number of caffeine-based products available on the market are creams.

In addition to the inputs given in example 1, other inputs are available as follows:

Anhydrous caffeine in powder marketed by INTERAXION

MULTIFLEX® G00A41 elastomer marketed by DOW CORNING.

The elaboration of a caffeine patch according to the invention proceeds in three steps.

Step 1: Preparation of the Active Solution

The preparation of the active solution passes by the solubilisation of the caffeine in the solvent mixture according to a ratio oxygenated solvent of dibasic esters of methylenic fatty acids/oxygenated methylenic solvent of 3/5.

Procedure:

In a 1 liter beaker, the following are successively added under stirring:

150 g ESTASOL®;
250 g ARLASOLVE® DMI;
25 g caffeine;
100 g refined coconut oil.

All is stirred for 20 minutes until the active solution becomes limpid. The said active solution is stable, that is, the caffeine does not recrystallise.

Step 2: Incorporation of the Active Solution into the Polymer Mixture PEBAX®/PEARLTHANE® D15N70 according to a ratio of 1/2

Procedure:

Preheat the DRAIS horizontal mixer having a volume of 20 liters, to 95° C.;

Introduce 1000 g of PEBAX® granules and 2000 g of PEARLTHANE® D15N70 granules in it;

Stir at 80 rpm until the real temperature of the polymer granules reaches 90° C.;

Still stirring, add drop by drop 525 g of active solution to the mixer;

Let the active solution incorporate for at least 15 min into the polymer granules until they become dry and unsticky;

Lower the temperature to 20° C., and stir at 50 rpm;

Still stirring at 50 rpm, add 100 g of pearly white colouring agent;

Still stirring at 50 rpm, add 500 g of MULTIFLEX® G00A41;

Stop stirring after 5 minutes;

The resulting polymer granules loaded with the lipophilic caffeine solution are collected.

Step 3: Forming a Patch Intended to be Applied to the Thighs.

The same equipment is available as in example 1. The mounted moulds have four imprints-moulds in the shape of a parallelogram 7 centimeters long, 4 centimeters wide and 2 millimeters deep.

The injection temperature chart from the hopper to the nozzle is as follows: 105° C., 125° C., 125° C., 25%.

The obtained patches with 0.6% caffeine and a slimming effect are very flexible. MULTIFLEX G00A41 brings the essential flexibility to the said patches. They can be applied directly to the skin at the level of the thighs to fight against orange skin. The said patches can be associated with a panty for a more intimate application against the skin.

The invention claimed is:

1. A vehicle-free method of loading a naturally crystalline substance solubilized by a solvent mixture in a lipophilic medium into a mixture of polymer granules for forming a plasticizer-free polymer support for long-term controlled release of the naturally crystalline substance in a stable solubilized state, wherein said method ensures the permanent non-crystallization on a surface of said polymer support, said method comprising the steps of:
    a) preparation of said solvent mixture which comprises an oxygenated solvent of dibasic esters of methylenic fatty acids and an oxygenated methylenic cosolvent;
    b) solubilization of said naturally crystalline substance in said solvent mixture of step a) to obtain a stable solution of said naturally crystalline substance;
    c) addition of a vegetable oil in said stable solution of step b) to obtain an active lipophilic solution;
    d) incorporation of said active lipophilic solution obtained in step c) into a mixture of polymer granules comprising a polyether block amide (PEBA) and a thermoplastic polyurethane elastomer (TPU) to form a polymer mixture loaded with said naturally crystalline substance in said stable solubilized state;
    e) forming of said polymer support loaded with said naturally crystalline substance in a stable solubilized state by shaping said mixture of polymer granules loaded with said naturally crystalline substance obtained in d).

2. The method according to claim 1, wherein a ratio of the two components of the solvent mixture in the order solvent/cosolvent varies between 38/62 and 90/10.

3. The method according to claim 1, wherein a concentration threshold of the naturally crystalline substance is increased by solubilizing in said solvent mixture at a temperature between room temperature and 45° C.

4. The method according to claim 1, wherein a ratio of the polymer mixture comprising PEBA/TPU varies between 80/20 and 40/60.

5. The method according to claim 1, wherein said solubilized naturally crystalline substance is selected from the group consisting of an insecticide a pesticide, a cosmetic, and a drug.

6. The method according to claim 1, wherein said technical additives comprise coloring agents and/or structure polymers.

7. The method according to claim 1, wherein a ratio of incorporation of said naturally crystalline substance varies between 0.25% and 20% by weight of the support.

8. A polymer support for long-term controlled release of a naturally crystalline substance in a stable solubilized state, wherein a permanent non-crystallization state on a surface of said polymer support is only assured when said naturally crystalline substance is solubilized in a solvent mixture composed of an oxygenated solvent of dibasic esters of methylenic fatty acids and an oxygenated methylenic cosolvent forming an active lipophilic solution by adding a vegetable oil, this active lipophilic solution being incorporated into a mixture of polymer granules composed of a polyether block amide (PEBA) and a thermoplastic polyurethane elastomer (TPU), wherein said polymer support is obtained by molding said mixture of polymer granules loaded with said crystalline substance.

9. The polymer support of claim 8, wherein a ratio of the two components of the solvent mixture in the order solvent/cosolvent varies between 38/62 and 90/10.

10. The polymer support of claim 8, wherein the ratio of the polymer mixture in the order PEBA/TPU varies between 80/20 and 40/60.

11. The polymer support of claim 8, further comprising a technical additive.

12. The polymer support of claim 8, wherein said polymer support has a storage capacity between 0.25% and 20% by weight of a naturally crystalline substance with respect to the total weight of the said support.

13. The polymer support of claim 8, wherein said polymer support is in the shape of a collar, a medallion, an ear tag for animals, a bracelet, a patch, a pack, or a block.

14. The method of claim 1, further comprising addition of a technical additive to said polymer mixture loaded with said naturally crystalline substance.

15. The method of claim 2, wherein said wherein the ratio of the two components of the solvent mixture in the order solvent/cosolvent varies between 45/55 and 75/25.

16. The method of claim 4, wherein said ratio of the polymer mixture in the order PEBA/TPU varies between 55/45 and 45/55.

17. The method of claim 5, wherein said insecticide or pesticide is selected from the group consisting of a pyrethroid, a formamidine and a carbamate, or a combination thereof.

18. The method of claim 5, wherein said cosmetic is an alkaloid.

19. The polymer support of claim 9, wherein said ratio of the two components of the solvent mixture in the order solvent/cosolvent varies between 45/55 and 75/25.

20. The polymer support of claim 10, wherein the ratio of the polymer mixture in the order PEBA/TPU varies between 55/45 and 45/55.

* * * * *